United States Patent [19]
Dyck et al.

[11] Patent Number: 4,549,551
[45] Date of Patent: Oct. 29, 1985

[54] HEART RATE DETECTOR

[75] Inventors: Walter R. Dyck; Ronald A. Eirich, both of Medicine Hat, Canada

[73] Assignee: Her Majesty the Queen in right of Canada, as represented by the Minister of National Defense, Ottawa, Canada

[21] Appl. No.: 553,116

[22] Filed: Nov. 18, 1983

[30] Foreign Application Priority Data

Nov. 24, 1982 [CA] Canada .................................. 416203

[51] Int. Cl.<sup>4</sup> .............................................. A61B 5/02
[52] U.S. Cl. ...................................... 128/689; 128/715
[58] Field of Search ............... 128/680, 687, 689, 690, 128/695, 700, 701, 706, 715

[56] References Cited

U.S. PATENT DOCUMENTS

| 3,581,735 | 6/1971 | Gentner et al. | 128/715 |
| 3,750,644 | 8/1973 | Ragsdale | 128/706 |
| 4,120,296 | 10/1978 | Prinz | 128/690 |
| 4,362,164 | 12/1982 | Little et al. | 128/715 |
| 4,436,096 | 3/1984 | Dyck et al. | 128/689 |
| 4,458,692 | 7/1984 | Simson | 128/705 |

Primary Examiner—William E. Kamm
Attorney, Agent, or Firm—Cushman, Darby & Cushman

[57] ABSTRACT

An electronic heart sound detector in which a transducer detects the two primary heart beats of the heart cycle to produce a signal which is converted to a digital signal, filtered and the intervals between adjacent transitions determined and stored. The intervals are compared with previous values, successive values added if found substantially different and the stored or added values displayed if substantially the same as a previous correct value. The functions may be carried out by a microprocessor.

7 Claims, 6 Drawing Figures fig.4A.

HEART RATE DETECTOR

This invention relates to a heart rate detector and, particularly, to a portable device which produces an audio indication of the heart sounds and a visual digital display of the heart rate of a patient.

BACKGROUND OF THE INVENTION

As is well known, medical personnel must listen to and determine the heart rate of a patient in order to determine the condition of the patient. Standard or electronic stethoscopes are normally used to listen to a patient's heart and are formed with a detector which must be placed in contact with the skin of the chest of a patient. The heart rate is often determined by counting the number of heart beats over a period of time and multiplying the count by an appropriate factor.

There are situations, such as in the case of burn or trapped victims, in which the patients clothing cannot be removed. In such situations, it is necessary to listen to the patient's heart through the patient's clothing. This factor coupled with the likelihood of high background noise results in obscured heart sounds and considerable difficulty in accurately determining a patient's heart rate.

Standard stethoscopes require skin contact and therefore cannot be used in such a situation while electronic stethoscopes tend to produce high background electrical noise which further obscures the heart sounds. Neither provide a digital reading of heart rate. There are devices which can accurately measure heart rate from a patient's electrocardiograph but they tend to be bulky, heavy, expensive, require skin contact and complicated in use. Thus, there is a need for an easily operated, light, portable device which accurately reproduces heart sounds through several layers of clothing and provides a digital reading of heart rate.

Apart from distinguishing between heart sounds and extraneous or background noise, a device which measures heart rate must also account for the different heart sounds of which a heart cycle is comprised. More specifically, it is known that a heart beat or cycle is primarily comprised of two relatively closely spaced heart sounds. Assuming all extraneous and background noise could be removed and both heart sounds detected for each heart cycle, the heart rate could readily be determined simply by determining the time interval or period between three adjacent sounds and converting the period to a beats per minute (BPM) heart rate count. In practice, it is not possible to eliminate all background noise and detect both heart sounds of all cycles and thus this approach may provide inaccurate heart rate displays.

SUMMARY OF THE INVENTION

The present invention provides a light, portable, easily operated heart rate detector which provides an audio indication of heart sounds and an accurate digital display of heart rate.

One aspect of the present invention relates to the means by which extraneous and background noise is separated from heart sounds. This aspect of the invention provides a transducer for producing electrical signals corresponding to heart sounds, means for sampling the electrical signals at a predetermined sampling frequency and producing a series of digital signals, digital filter means for producing a series of filtered digital signals, and means for detecting and displaying the heart rate from the series of filtered digital signals. The digital filter means enables much more effective elimination of spikes and sounds having frequencies not characteristic of heart sounds than is possible with linear filters.

Another aspect of the present invention relates to the means which detects heart sounds and determines the heart rate. This aspect of the invention provides means for detecting the time interval between adjacent heart sounds and produces a heart rate signal which is proportional to the time period when two adjacent periods are substantially the same or to the sum of two adjacent periods when the two adjacent periods are substantially different.

Thus, when two heart sounds in a heart cycle are detected, the device determines the time interval or period between the first and second sounds and the time interval or period between the second sound and the first sound of the next cycle. Normally, heart sounds are relatively closely spaced and in particular are within about ¼ of the period of a heart cycle apart. Accordingly, the second period may be three times longer than the first period. Thus, the detection of two such intervals is a detection of two heart sounds of a heart cycle. On the other hand, when one of the heart sounds of one cycle is too weak to be detected, the time interval between the last sound of the preceding cycle and the first sound of the next cycle will be substantially greater than the last period of the preceding cycle and substantially the same as the period of the previous heart cycle period. Thus, the BPM count is simply determined by converting the period to a BPM frequency.

BRIEF DESCRIPTION OF THE DRAWINGS

These and other features of the invention will become more apparent from the following description in which reference is made to the appended drawings, wherein.

DETAIL DESCRIPTION OF THE INVENTION

Figure 1:
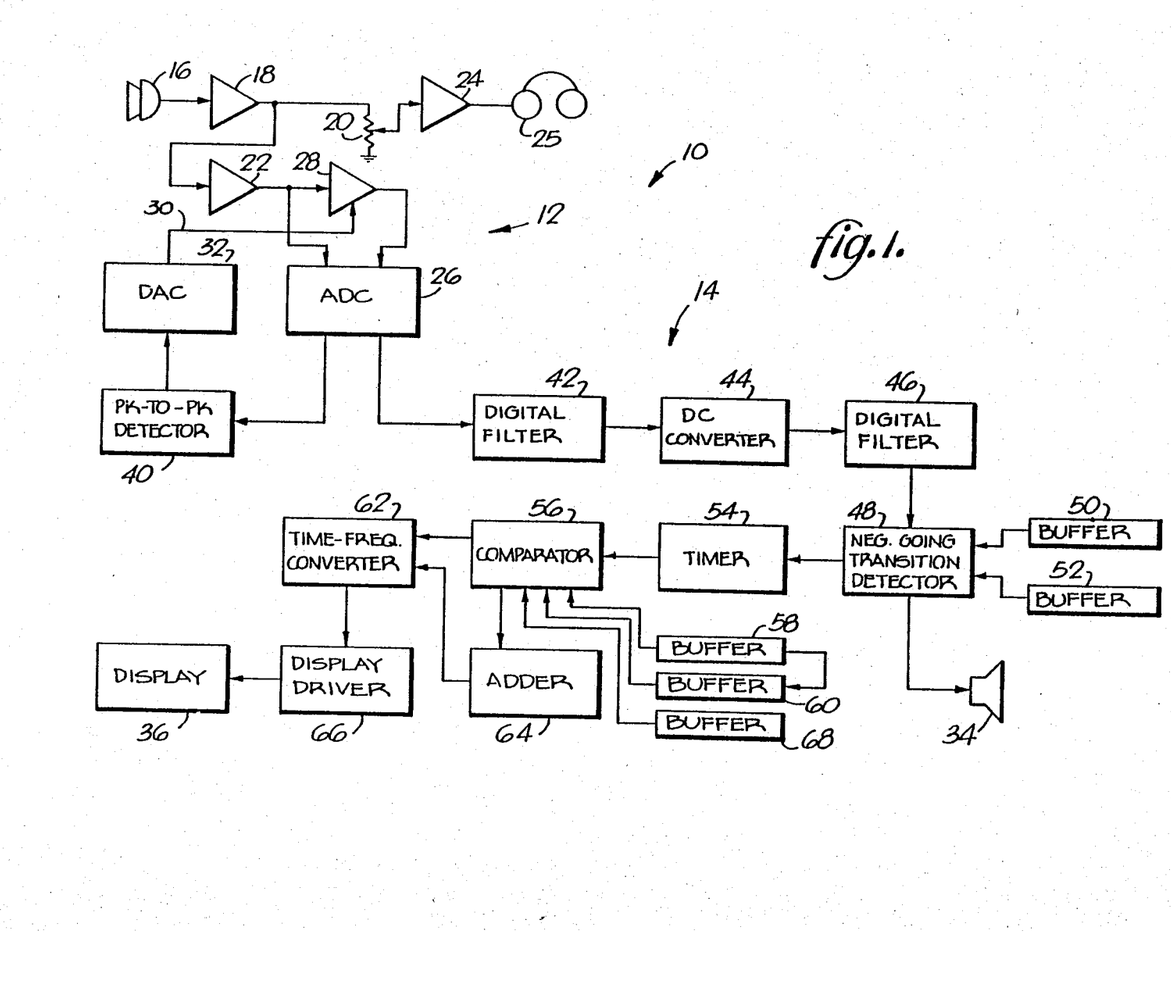
FIG. 1 is a block diagram of one embodiment of a heart rate detector according to the present invention.

The heart rate detector 10 of the present invention is illustrated in the form of a block diagram in FIG. 1 of the drawings. The heart rate detector includes a linear or analog circuit portion generally designated by reference numeral 12 and a digital portion generally designated by reference numeral 14.

Analog portion 12 of the detector includes a pulse-audio transducer or microphone 16 which converts sound and pressure waves into electrical signals and applies the signals to an amplifier 18. Amplifier 18 amplifies the weak microphone signals and applies amplified signals to a volume control 20 and a low pass filter 22. The output of volume control 20 is fed to a second amplifier 24 which serves as a power amplifier for the earphones of a headset 25 worn by an operator.

Low pass filter 22 is an anti-aliazing filter which is provided to avoid problems which may be associated with digital filters incorporated in digital circuit 14. The output of filter 22 is connected to an analog-to-digital converter (ADC) 26 and to a variable gain amplifier 28 whose output is also connected to ADC 26 as shown. The gain of amplifier 28 is directly proportional to the current fed to it along line 30 from a digital-to-analog (DAC) converter 32 of digital circuit 14.

Amplifier 28 is part of an automatic gain control as will be explained with greater particularity later. Automatic gain control is desirable in order to compensate for varying input levels to the transducer inasmuch as in some instances the transducer may be applied directly to the skin of a patient. In these instances, a low level of gain is sufficient. In other instances, the transducer must detect signals through several layers of clothing and thus a higher level of gain is required. Thus, amplifier 28 maintains the amplitude of the waveform input to ADC 26 within predetermined levels at all times.

An additional audio indication is provided in the form of a beeper 34.

The digital portion 14 of the detector carries out two primary functions. Firstly, on the basis of the signal received from filter 22, it determines the magnitude of the current which is fed to amplifier 28 in order to maintain the output of amplifier 28 substantially constant. Secondly, it detects heart sounds, determines the current heart rate and displays the heart rate on a digital display 36. In addition, the circuit is arranged to detect only those signals which exceed a predetermined threshold level so as to minimize effects of noise in the signal. The second heart beat of a heart cycle may fall below the threshold level. The circuit is arranged to provide the correct heart rate notwithstanding a failure to detect the second heart beat of a cycle.

The first primary function of the digital circuit is effected by ADC 26, peak-to-peak detector 40 and DAC 32. ADC 26 samples the unamplified output of filter 22 at a predetermined sampling frequency and applies a series of digital signals to peak-to-peak detector 40. Detector 40 detects peak-to-peak signals and, in response thereto, generates a digital signal which is representative of the magnitude of the current to be applied to amplifier 28 in order to maintain its output waveform substantially constant. That signal is applied to DAC 32. DAC 32 converts the digital signal to a linear or analog signal and, in particular, to the desired current and applies the current to amplifier 28 along line 30.

ADC 26 samples the output of amplifier 28 at a predetermined sampling frequency and produces a series of digital signals representative of the output waveform of amplifier 28. A sampling frequency of 100 Hz is considered adequate for the purposes of the present invention.

The digital portion of the detector is based upon the detection of basic frequencies which occur in all heart sounds. The band of frequencies that is used for heart sound detection is in the region of 16 to 42 Hz. The digital portion of the circuit includes a pair of digital filters which provide a steep roll-off rate so that out-of-band frequencies and spikes do not cause erroneous readings. The digital portion of the circuit is also arranged to convert the signals to DC equivalents. Thus, the series of digital signals, representative of the output of amplifier 28, is applied to a first finite impulse response digital filter 42 having a passband of about 16 to 42 Hz. The series of filtered digital signals are then applied to DC converter 44 which in turn applies the resultant series of signals to a second finite impulse response digital filter 46 having a passband of from 0-3 Hz.

Figure 2:
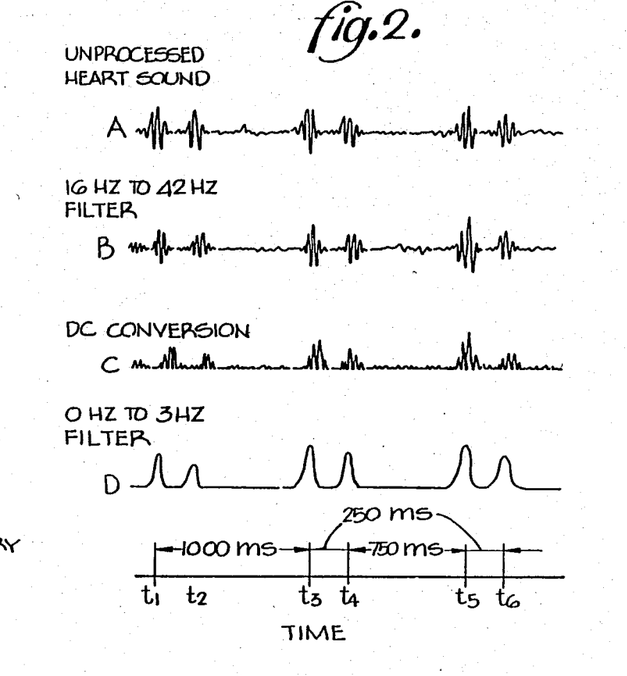
FIG. 2 is a diagrammatic representation of electrical signal waveforms of the heart signals at various stages in the detector.

FIG. 2 diagrammatically illustrates the various waveforms of the signal at various stages in the device. Waveform A represents the output of amplifier 28. Waveform B represents the output of filter 42. It will be noted that it is somewhat different from waveform A in that various frequencies have been eliminated. Waveform C represents the output of converter 44 while waveform D represents the output of digital filter 46. The output of filter 46 contains only signals representative of heart rate frequencies. The likelihood is small that sounds other than heart sounds in the vicinity of the patient would have the characteristic frequencies of the human heart. Accordingly, there is a high degree of certainty that the signal indicated by waveform D, the output of filter 46, represents the heart sounds of the patient.

The output of filter 46 is applied to a detector 48 which includes at least a first buffer 50 for storing the most recent sample of the series of filtered digital signals and a second buffer 52 for storing the second most recent sample of the series of filtered signals. Detector 48 compares these two most recent signals and applies an output signal to a timer 54 whenever it detects a negative going transition. A negative going transition condition exists when the value of buffer 50 is less than the value of buffer 52. This condition is indicative of a local maximum value of waveform D and will occur whenever the first or second heart sound of a heart cycle is detected. In addition to applying a signal to timer 54, detector 48 applies a signal to beeper 34 so as to provide an audio indication of a detected heart sound.

Timer 54 applies to a comparator 56 a signal which represents the time interval or period between two negative going transitions as detected by detector 48. Associated with comparator 56 are a buffer 58 for storing the most recent period, a buffer 60 for storing the second most recent period and a buffer 68 for storing the last correct period of the heart rate. In order to appreciate the operation of comparator 56 and its associated buffers, it is important to understand two characteristics of the heart cycle. First, each heart cycle has two primary heart beats which, as previously mentioned, are relatively closely spaced in relation to the period of the heart cycle. Thus, the first period of a heart cycle can readily be distinguished from the second period and both of these can readily be distinguished from the period of a heart cycle. Secondly, the period of a heart cycle does not change significantly from one cycle to the next. Thus, it is possible to determine whether a determined heart rate is correct by comparing it with its preceding heart rate period.

Comparator 56 compares the content of buffers 58 and 60 and, if they are determined to be substantially the same, applies the content of buffer 58 to a time-to-frequency converter 62 and stores this value in buffer 68. If, on the other hand, the contents of buffers 58 and 60 are determined to be substantially different, the contents of buffers 58 and 60 are added together in adder 64 and the sum is compared against the contents of buffer 68. A sum which is substantially the same as the content of buffer 68 indicates that the first and second periods of a heart cycle have been detected and the sum of the two periods is the period of a heart cycle. The sum is then stored in buffer 68 and a signal representing the sum is applied to converter 62 for display on display 36. If the sum is found to be substantially different from the contents of buffer 68, the sum is disregarded and the display is not altered.

With further reference to FIG. 2, detector 48 applies a signal to timer 54 upon receipt of the sample following the sample taken at $t_1$. Timer 54 terminates counting the previous period and commences timing the next period. Assuming that the pulse at time $t_2$ is not detected because its amplitude falls below the previously discussed threshold level, timer 54 will continue until the next negative-going transition is detected at time $t_3$. At that time, detector 48 applies a signal to timer 54 to terminate counting that period and commence counting the next period. The period corresponding to the time interval between $t_1$ and $t_3$, 1000 ms, is input to buffer 58 while the preceding period is shifted to buffer 60. For the purposes of this description, it will be assumed that the preceding heart cycle period was substantially equal to 1000 ms and that this value is stored in buffer 68.

Comparator 56 compares the contents of buffers 58 and 60 and determines that the two are substantially the same, i.e., 1000 ms. Thus, comparator 56 applies a signal corresponding to this period to converter 62, which produces a signal corresponding to a heart rate of 60 BPM and stores the contents of buffer 58, 1000 ms, in buffer 68.

When the sample following the sample taken at time $t_4$ is detected by detector 48, timer 54 is signalled and the contents of buffer 58 are shifted to buffer 60 while the period between $t_3$ and $t_4$, 250 ms, is stored in buffer 58. Comparator 56 now compares the contents of buffers 58 and 60 and finds that they are not equal. The contents of the two buffers are then added together in adder 64 and the sum, 1250 ms, is compared with the contents of buffer 68. Since the results are not substantially the same, no signal is applied to converter 62 and, thus, the display is not altered.

When the sample following that taken at time $t_5$ is reached, detector 48 signals timer 54 which, in turn, applies the period between $t_4$ and $t_5$, 750 ms, to buffer 58 and the contents of buffer 58, 250 ms, are shifted to buffer 60. Comparator 56 compares the contents of buffers 58 and 60 and determines that they are not substantially the same and, accordingly, the contents of the two buffers are added in adder 64 and the sum, 1000 ms, is compared against the contents of buffer 68. Since the contents of buffer 68 is also 1000 ms, a signal representing the sum of the contents of buffers 58 and 60 is applied to converter 62 which converts the period to a heart rate, 60 BPM, and digital display 36 is updated.

Figure 3:
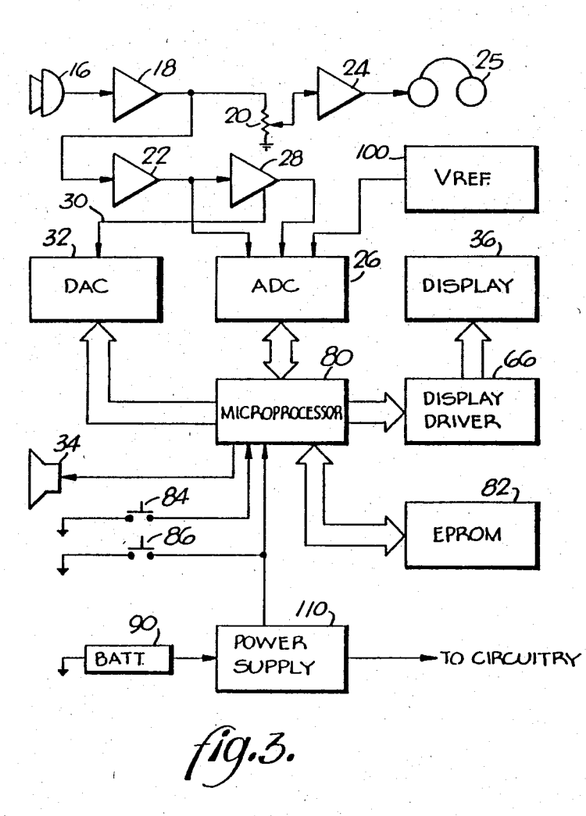
FIG. 3 is a block diagram of a preferred embodiment of a heart rate detector according to the present invention.

FIG. 3 illustrates in block diagram form a preferred form of the invention. This circuit is substantially the same as the preceding circuit except that the two digital filters 42 and 46, DC converter 44, detector 48 and its buffers, timer 54, comparator 56, its associated buffers 58, 60 and 68 and adder 64, and converter 62 are incorporated in a microprocessor 80 which operates under the control of an erasable programmable read only memory (EPROM) 82. In addition, microprocessor 80 monitors a beep control switch 84 and a power switch 86 and controls a power supply circuit 110 having a battery power supply 90, as will be explained later.

Figure 4A:
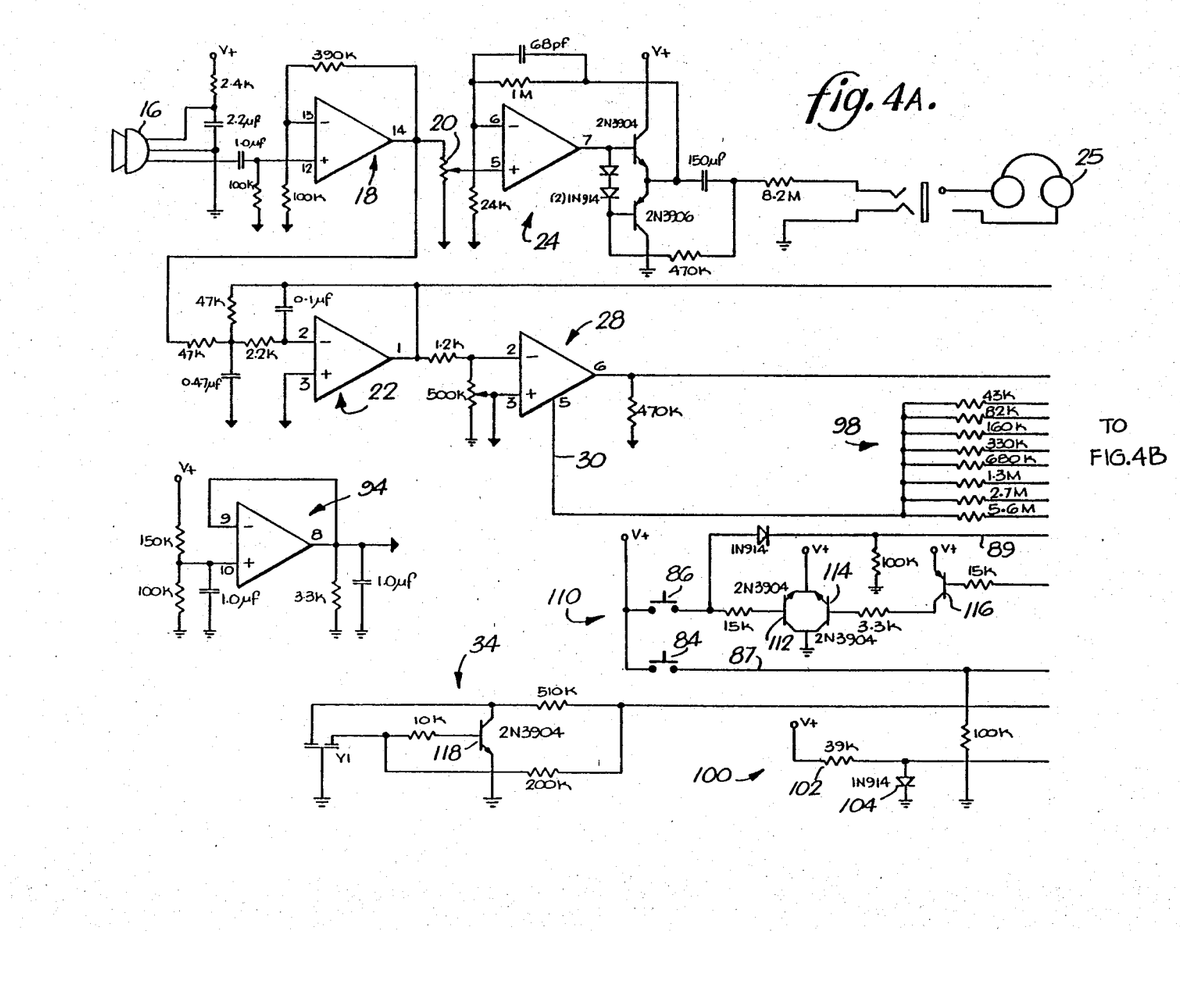
FIGS. 4A and 4B are schematic diagrams of an electrical circuit of a preferred embodiment of a heart rate detector according to the present invention.
Figure 4B:
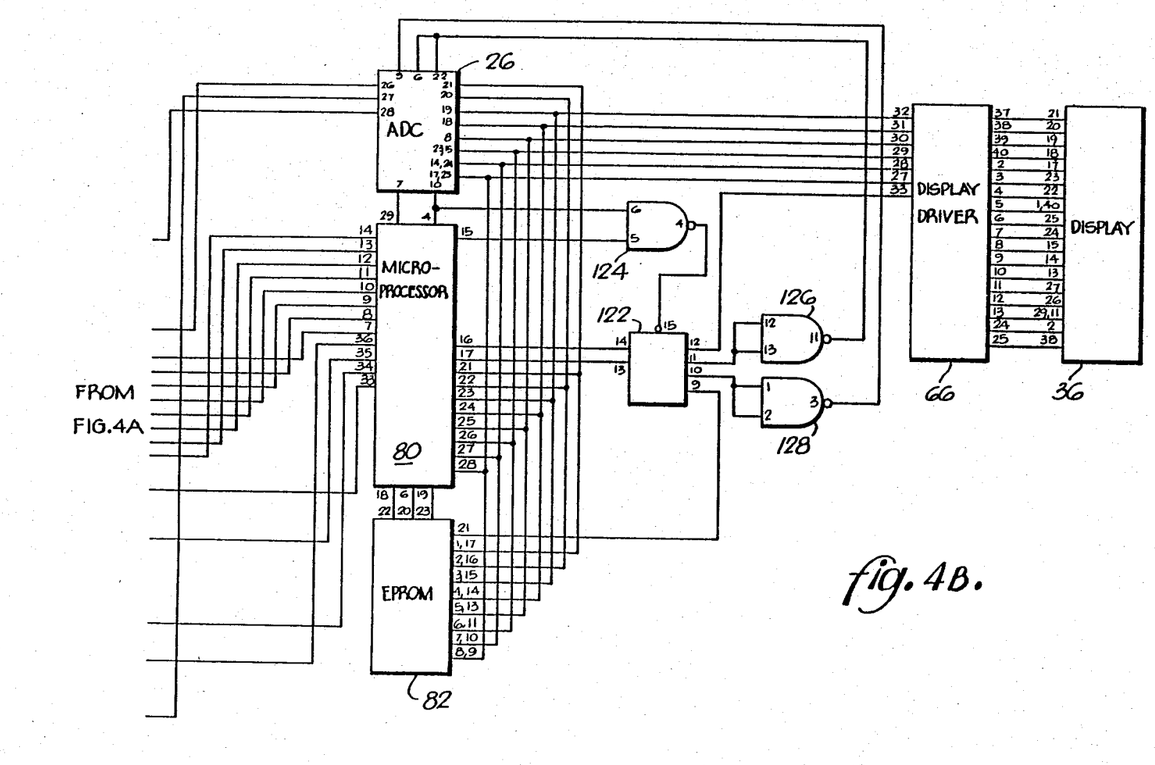

FIGS. 4A and 4B are an electrical schematic representation of a preferred form of the heart rate detector of the present invention. Transducer 16 is of conventional construction and connected to a source of power and amplifier 18. Amplifier 18 is formed by one amplifier of a quad-amp type LM 2902N having a gain of 4. The other amplifiers of this component form low pass filter 22, filter 24 and an amplifier 94 which together with its associated components generates a voltage of 2 volts used as a false ground to bias input levels to the various amplifiers in the detector circuit. Amplifier 24 and its associated components constitute the headphone power amplifier and has a gain of approximately 40, a frequency response of 40 to 2300 Hz and a power output of 35 mw into 8 ohms.

Filter 22 formed by the illustrated components has a 25 Hz upper cut-off frequency and a gain of 1 in the passband. As mentioned earlier, this filter is used to eliminate aliazing problems encountered with the digital filters implemented in microprocessor 80. The output of filter 22 is connected to pin 28 of ADC 26 and to pin 2 of amplifier 28 whose output is connected to pin 26 of ADC 26. Amplifier 28 is an operational transconductance amplifier (OTA) type CA3080AF and is used as a variable gain amplifier. Its gain is adjustable from 1 to 255 upon application of an appropriate current to pin 5 from line 30. Amplifier 28 is one part of an automatic gain control of which the other parts are a portion of microprocessor 80 and a summing network 98. Summing network 98 constitutes DAC 32. More specifically, DAC 32 is in the form of an 8-bit summing network of eight resistors, in parallel, connected to pins 7-14 of port A of microprocessor 80. Under software control, microprocessor 80 detects the peak-to-peak value of the signal applied to pin 28 of ADC 26, which signal originates from filter 22, and applies five volts to those resistors of the summing network which will provide the current in line 30 resulting in the desired gain in OTA 28 and a substantially constant output waveform therefrom.

A circuit 100, including a resistor 102 and diode 104, generates a 0.5 volt reference signal which is applied to pin 27 of ADC 26. This voltage is relatively independent of the supply voltage and is used with the ratiometric conversion properties of ADC 26, described in greater detail later, to provide a low battery indication to the microprocessor.

A power supply circuit 110 includes transistors 112, 114 and 116 and other associated components as shown. The base of transistor 116 is connected to pin 35 of the microprocessor. When the power switch 86 is depressed, transistor 112 is turned "on" thereby activating the balance of the circuit. Upon activation of the microprocessor, the microprocessor applies a low voltage to pin 35 so as to maintain itself in an "on" condition. When the microprocessor determines that the power should be turned "off", such as when switch 86 is once again depressed, the microprocessor applies a high voltage to pin 35. Lines 87 and 89 connect the downstream side of switches 84 and 86 to pins 33 and 34 of the microprocessor. The microprocessor monitors these pins and either activates or deactivates power supply circuit 110 and beeper 34 depending upon the state of their corresponding switches.

Beeper 34 is connected to pin 36 of the microprocessor and is formed by a transistor 118 and the components shown. The circuit is activated whenever pin 36 goes positive.

The description now turns to the digital portion 14 of the device.

ADC 26 is of type ADC 0808CCN having eight input pins, of which only three are used, and an analog multiplexer which can select any one of the eight inputs and route it to the main converter block. Pins 7 and 10 of ADC 26 are respectively connected to pins 29 and 4 of microprocessor 80. To initiate a conversion, the microprocessor applies the appropriate multiplexer address to ADC 26. Upon receipt of an address, the corresponding one of the three inputs will be selected and conversion will commence. The ADC takes no longer than about 100 μs to complete a conversion and, upon completion of conversion, pin 7 of the ADC goes high to signal the microprocessor.

The microprocessor is an 8-bit CMOS processor of type MC146805E2. The microprocessor operates under a program stored in a CMOS 1204×8-bit EPROM element 82 type IM6658IJG. CMOS is preferred in order to maintain power consumption as low as possible.

Figure 5:
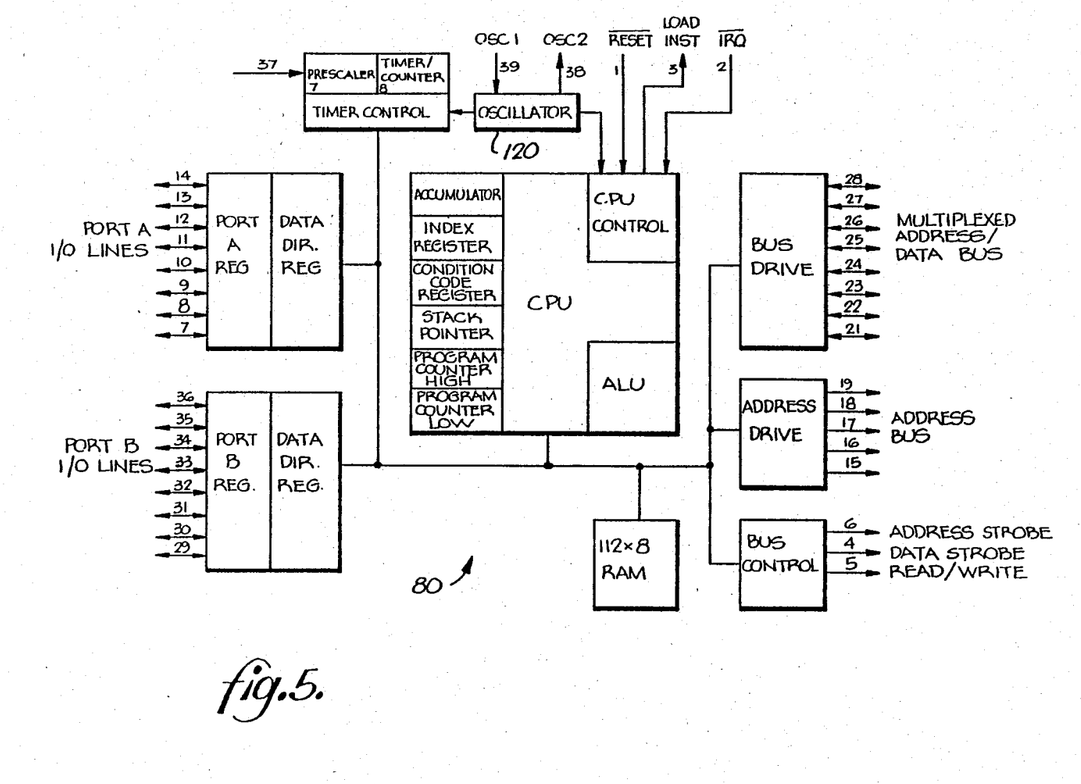
FIG. 5 is a block diagram of a microprocessor illustrated in FIG. 4B.

As shown in FIG. 5, the processor includes two ports A and B. Port A drives the current summing resistors of the summing network while port B is connected to power supply circuit 110 and beeper 34, as already explained. Ports A and B are fully programmable which means that the ports can be programmed for input and/or output by using its data direction registers. The microprocessor also includes a timer/counter which is used to generate the 100 Hz (or 10 ms) interrupt or sampling signals. An oscillator module 120 in the microprocessor chip is connected to a 4.00 MHz crystal whose frequency is divided by 5 to produce a 0.8 MHz cycle rate. The lower 8-bits of the address bus and the data bus are multiplexed to reduce the number of lines required. The non-multiplexed address lines are used for address decoding. The bus control lines are used to provide synchronization with the peripheral components such as the EPROM. The RAM is used to store temporary values such as the ADC input data and the like. When the processor is interrupted by the timer/counter, the processor samples the input waveform from the ADC, monitors the front panel keys and makes a display update if appropriate.

Components 122, 124, 126 and 128 are address decoders. Decoder 122 is of type CD4011AE while decoders 124, 126 and 128 are type MC14556B. These components are connected to the ADC, microprocessor, EPROM and display driver as shown and in accordance with manufacturer's instructions.

Display driver 66 is of type ICM7211AMIPL. It receives the microprocessor signals and drives liquid crystal display 36. A liquid crystal display is preferred because of its low power consumption and high visibility in sunlight. The display uses a 3½ digit display with a low battery indication and signs. The "minus" sign is used to provide a visual indication of heart pulse.

In view of the foregoing, it is not believed necessary to describe the software under which the microprocessor operates or further particulars of the pin connections of the various components. It is believed that those to whom the specification is addressed would have no difficulty in providing an appropriate program or interconnecting the components. A representative program is appended hereto.

It is also believed that finite impulse response digital filters are well known to those addressed by this specification. Reference may be had to "THEORY AND APPLICATION OF DIGITAL SIGNAL PROCESSING" by Rabener and Gold for general background theory relating to such filters. The appended program includes appropriate digital filter subroutines.

It is also to be understood that while the preferred form of the present invention contemplates 2 microprocessor, the invention can also be constructed of a fully hard-wired electrical circuit utilizing currently available integrated circuits and other associated components.

```
            BNE     CLRAM
            LDA     #0EH        INITIALIZE TIMER
            STA     TIMC        STORE IN TIMER CONTROL BYTE
IDLE        CLI                 ENABLE INTERUPT PROCESSING
            BRA     IDLE        WAIT FOR TIMER TO COUNT TO 0
.GO         LDA     #125        SET TIMER FOR 10 MS DELAY
            STA     TIM         INITIALIZE TIMER FOR 10 mS COUNT
            BCLR    7,9         CLEAR TCR TIMER INT REQUEST BIT
            LDX     #2FH
STORE2      LDA     0FH,X       PUT DATA IN BUFFER
            STA     10H,X
            DEX
            BNE     STORE2
            LDA     #2          GET A/D DATA CHN 2
            JSR     AD
            CMP     LOW         IS THIS THE LOWEST VALUE
            BHI     LOWFND
            STA     LOW         NO IT ISNT STORE ANOTHER NEWEST VALUE
            CLR     HI          CLEAR TEMPPEAK VALUE
            BRA     CAP
LOWFND      SUB     LOW         LOWEST VALUE WAS FOUND - GET PEAK VALUE
            CMP     HI          IS IT HIGHER THAN LAST PEAK VALUE
            BLO     HIFND
            STA     HI          YES IT IS! STORE MOST RECENT VALUE
            BRA     CAP
```

```
HIFND    CLR    LOW           ;SET LOW TO OFFH
         DEC    LOW
OOUS     TAX
         LDA    #OFFH
         STA    COF+1
         CLRA
         JSR    DIVD
         COMX
         CPX    AVC
         BLO    CAP
         STX    AVC
CAP      LDA    AVC+1
         SUB    AVC
         STA    AVC+1
         LDA    AVC
         SEC    #0
         STA    AVC
         COMA
         STA    4
         DEC    TIMER+1
         BNE    INTEST
         DEC    TIMER
         BEQ    OFF
INTEST   BRCLR  3,1,BPTST     ??IS THE POWERKEY HIT??
         BSET   7,PWRHIT      ; YES IT HAS SET FLAG
         LDA    #1
         BRA    SETBP1        NOW SET BEEP LENGTH
BPTST    BRCLR  2,1,BPTST1    ??IS THE BEEP ON/OFF KEY HIT??
         BSET   7,BPHIT       YES SET THE FLAG
SETBP    LDA    #20           SET BEEP INTERVAL TO .2 SEC
SETBP1   STA    CNT1
         BRA    HITFIN
BPTST1   TST    CNT1          ??IS BEEPER FINISHED??
         BNE    HITFIN
         BRCLR  7,PWRHIT,BPTST2  YES! IS PWRHIT FLAG ON
         CLR    PWRHIT        YES! CLR PWRHIT FLAG
         COM    PWRFLG        HAS FLAG BEEN TURNED ON?
         BNE    HITFIN
OFF      BSET   1,1           YES! POWER DOWN PROCESSOR
OFF1     BRA    OFF1
BPTST2   BRCLR  7,BPHIT,HITFIN   ??IS BEEP FLAG ON??
         COM    BPFLG         YES
         CLR    BPHIT
HITFIN   LDA    #1
         STA    VAR
         BCLR   0,1           TURN BUZZER OFF
         JSR    AD            GET A/D VALUE FOR VOLTAGE REF
         CMP    #30           ARE THE BATTERIES LOW?
         BLO    TICK
         BSET   3,VAR         SET LOWBATT BIT IN OUTPUT BYTE
TICK     TST    CNT1          IS TICK AND BUZZER CNTR TIMED OUT
         BEQ    OUT2
         DEC    CNT1          DECREMENT TICK AND BUZZER TIMER
         BRSET  7,BPHIT,ONBP
         BRCLR  7,BPFLG,NOBP
ONBP     BSET   0,1           BEEP BUZZER
NOBP     BCLR   0,VAR         SET TICK BIT IN OUTPUT BYTE
```

```
OUT2    LDA     VAR
        STA     1000H       TICK AND OR LOW BATT TO DISPLAY
        INC     CNT         INCREMENT COUNT
        BNE     FILTER      EXCEEDED 256 COUNTS
        DEC     CNT         YES - OUTPUT 00 IN DISPLAY
        CLRA
        JSR     CON
FILTER  CLRA                GET A/D VALUE CHANNEL 0 (OUTPUT FROM
        JSR     AD                  VARIABLE GAIN AMPLIFIER)
        ADD     #80H        BAND PASS FILTER INIT
        ASRA                DIVIDE INPUT BY 2
        LDX     #BPSTRT-1F00H
        STX     COF
        LDX     #BPEND-1F00H+1
        STX     COF1
        LDX     #2FH
        STX     VAR1
        LDX     #10H
        JSR     FILT
        TSTA                CONVERT AC WAVEFORM TO DC
        BPL     LOWPS
        NEGA
LOWPS   LDX     #LPSTRT-1F00H   LOW PASS FILTER INITIALIZATION
        STX     COF
        LDX     #LPEND-1F00H+1
        STX     COF1
        LDX     #3FH
        STX     VAR1
        LDX     #30H
        JSR     FILT
        BRSET   7,FLAG,LOWPK    -VE OR +VE GOING WAVEFORM
        CMP     PK              +VE GOING
        BLO     HPK
        STA     PK          STORE INTERIM VALUE
        BRA     OUT
HPK     BSET    7,FLAG      HIGH POINT FOUND
        LDA     LPK
        LDX     #0FFH       SET FLAG FOR -VE GOING
        STX     LPK
        SUB     PK          IS PK - PK VAL > 5
        NEGA
        STA     PTP
        CMP     #05H
        BLO     OUT         NO
        LDX     OPK         STORE NEW P-P VALUE
        LSRX
        CPX     PTP
        BLO     HPK2        IF NEW P-P < 1/2 OF OLD ABORT
        DEC     IGNR
        BNE     OUT
        STA     OPK
        LDA     #04
        STA     IGNR
        BRA     OUT
HPK2    STA     OPK
        LDA     #4
        STA     IGNR
```

```
              BSET    4,CNT1       RESET TICK LCD DISPLAY & BEEP TIMER
              LDA     LCNT         GET LAST COUNT FOR COMPARISON
              LSRA
              LSRA
              STA     LCNT1        STORE TOLERANCE
              ADD     LCNT         ADD(LAST COUNT + LAST COUNT/8)
              CMP     CNT          CMP CURRENT CNT ,TOL ADJUSTED LST CNT
              BLO     DISP         BRANCH IF OUT OF TOL
              LDA     LCNT         IF TEST GOOD TEST LOWER TOLERANCE
              SUB     LCNT1        GET (LAST COUNT-LAST COUNT/8)
              CMP     CNT          CMP CURRENT CNT AND LWR TOL LMT
              BHI     DISP         BRANCH IF OUT OF TOLERANCE
              LDA     CNT
DISP1         CMP     #0FFH        ?IS INTERVAL COUNTER OVERFLOWED
              BNE     AVG
AVG3          CLR     SYM          YES RESET SYMETRY FLAG
DISP2         LDA     CNT          UPDATE LAST COUNT
              STA     LCNT
              CLR     CNT          RESET INTERVAL COUNTER
              BRA     OUT
DISP          BRCLR   7,SYM,SYMM   WAS SECOND HRT SOUND FOUND BEFORE?
              LDA     CNT             YES IT WAS
              ADD     LCNT         ADD COUNT AND LAST COUNT
              STA     CNT          STORE IN INTERVAL COUNT
              BRA     DISP1
SYMM          BSET    7,SYM        SET SYMMETRY FLAG
              BRA     DISP2        POSSIBLE 2ND HEART SOUND FOUND
LOWPK         CMP     LPK
              BHI     UP           WAS THE BOTTOM OF THE WAVEFORM
              STA     LPK          BEEN FOUND
              BRA     OUT
UP            CLR     FLAG         YES IT HAS
              CLR     PK
OUT           RTI                  WAIT FOR INTERUPT FROM TIMER
AVG           TAX
              LDA     #70H         DIVIDE 6000 BY INTERVAL COUNT
              STA     COF+1           TO GET BPM
              LDA     #17H
              STA     TIMER        SET AUTO TURNOFF INTERVAL
              JSR     DIVD
              TXA
              BSR     CON          CONVERT BPM READING AND OUTPUT IT
              BRA     AVG3
CON           CLRX                 BINARY TO BCD CONVERSION
              CLR     VAR          X(BIN) TO SUM(MSD),X,A(LSD)
CON1          CMP     #0AH         IS A<10
              BLO     CON2         YES OUTPUT BPM READING
              SUB     #0AH         NO SUBTRACT 10 FROM A
              INX                  INCREMENT 10s COUNTER
              CPX     #0AH         IS X<10
              BLO     CON1
              CLRX                 NO CLEAR 10s COUNT
              INC     VAR          INCREMENT HUNDREDS COUNT
              BRA     CON1
CON2          ORA     #30H
              STA     1000H        OUTPUT LEAST SIG DIGIT
              TXA
              ORA     #20H
```

```
              STA    1000H        OUPUT TENS DIGIT
              LDA    VAR
              ORA    #14H
              STA    1000H        OUTPUT HUNDREDS DIGIT
              RTS
FILT          STX    VAR          FIR FILTER ROUTINE
              STA    X
              CLR    SUM          CLEAR FILTER OUTPUT VALUE
              CLR    SUM+1
LOOP          LDX    VAR
              LDA    X            GET DATA FROM BUFFER
              LDX    VAR1
              ADD    X            ADD ANOTHER BYTE FROM BUFFER
              LDX    COF
              CPX    COF1
              BEQ    DA
              LDX    1F00H,X      GET FILTER CO-EFFICIENT
              INC    COF
              INC    VAR
              DEC    VAR1
              BSR    MILT         MULTIPLY ADDED BUFFER DATA AND
MULT2         STA    MULT                    CO-EFFICIENT
              TXA
              ADD    SUM+1        UPDATE FILTER OUTPUT VALUE
              STA    SUM+1
              LDA    MULT
              ADC    SUM
              LDX    SUM
              STA    SUM
              TXA
              EOR    MULT         IS RESULT OUT OF RANGE
              BMI    LOOP
              TXA
              EOR    SUM
              BPL    LOOP
              LDA    #7FH         ?YES ADJUST IT
              BRSET  7,SUM,CORE
              ADD    #2
CORE          STA    SUM
DA            LDA    SUM
              RTS
DIVD          STX    COF          DIVISION ROUTINE
              LDX    #1           DIVIDE   A + COF+1 / X
DIVD1         ASL    COF+1
              ROLA
              BCS    DIVD3
DIVD2         CMP    COF
              BLO    DIVD4
DIVD3         SUB    COF
              CLC
DIVD4         ROLX
              BCC    DIVD1
              COMX                QUOTIENT IN X
              RTS
MILT          STA    MULT         MULTIPLY ROUTINE A*X=A(HI) & X(LOW)
              STX    MULT+1
              CLRA
              LDX    #80H
```

```
MULT1    ROR    MULT+1
         BCC    ADD
         SUB    MULT
SUB      ASRA
         RORX
         BCS    MILT1
         ROR    MULT+1
         BCS    SUB
         ADD    MULT
ADD      ASRA
         RORX
         BCC    MULT1
MILT1    RTS
AD       STA    1800H       A/D ROUTINE
AD1      BRSET  7,1,AD1     GET A/D VALUE FROM CHANNEL IN A
AD2      BRCLR  7,1,AD2
         LDA    1400H
         RTS
* 0-0 .16,0.2-0.38,0.42-0.5 EDGES,38,1,38 HEIGHTS
         ORG    1FE0H
BFSTRT   FCB    0F9H,004H,0FH,0F0H    BANDPASS CO-EFFICIENTS
         FCB    0F9H,0AH,0FCH,014H
         FCB    0F5H,0E6H,00CH,0FEH
         FCB    38H,0EEH,81H
BFEND    FCB    63H
LFSTRT   FCB    16H,1FH,30H,44H       LOWPASS CO-EFFICIENTS
         FCB    58H,6AH,78H
LFEND    FCB    7FH
         ORG    1FF8H       TIMER INTERUPT VECTOR
         FDB    GO
         NOP
         NOP
         NOP
         NOP
         ORG    1FFEH       RESET VECTOR
         FDB    1C00H
```

The embodiments of the invention in which an exclusive property or privilege is claimed are defined as follows:

1. An electronic heart rate detector, comprising:
a transducer for converting sounds to electrical signals;
a first amplifier for amplifying said electrical signals and producing first amplified electrical signals;
a second amplifier for amplifying said first amplified electrical signals, a second transducer for converting said second amplified electrical signals to sounds;
a low pass filter having an upper cut-off frequency of 25 Hz for filtering said first amplified electrical signals and providing filtered electrical signals;
a variable gain amplifier for amplifying said filtered electrical signals and providing amplified filtered electrical signals, said variable gain amplifier maintaining the amplitude of said amplified electrical signals within predetermined limits;
means for sampling said filtered electrical signals and said amplified filtered electrical signals at a predetermined sampling frequency and producing a first series of digital signals representative of said filtered electrical signals and a second series of digital signals representative of said amplified filtered electrical filters;
means responsive to said first series of digital signals for detecting the peak-to-peak value thereof and providing a gain control signal to said variable gain amplifier;
first digital filter means for filtering said second series of digital signals and providing a series of once filtered digital signals, said first filter means having a passband of about 16 Hz to 42 Hz;
converter means for converting said series of once filtered digital filters to a series of DC signals;
second digital filter means for filtering said series of DC signals and providing a series of filtered DC digital signals;
a first comparator for comparing each signal of said series of filtered DC signals with its immediately preceding signal and producing a clock signal indicative of a negative-going transition when the magnitude of said most recent signal is less than the magnitude of its immediately preceding signal;
timer means responsive to said first detector means output signal for producing signals representative of the time interval between negative-going transitions;

second comparator means for comparing a most recent timer means output signal against immediately preceding output signal and providing a first output signal representative of a heart rate when said most recent timer means signal and its immediately preceding signal are substantially the same and a second output signal representative of the sum of said timer means output signals when said timer means signals are substantially different; and means for displaying said first or said second comparator means output signals as a BPM heart rate count.

2. An electronic heart sound detector comprising:

a transducer for producing an electrical signal in response to each of the two primary heart beats of the heart cycle;

means for converting the electrical signals produced by said transducer into a sequence of digital signals;

means for digitally filtering the converted signals;

first and second buffers;

means for determining and storing in said first buffer the time interval between the last two detected signals defining the most recent period and in said second buffer the time interval between the second and third last detected signals defining the second most recent period;

means for comparing the stored periods in said first and second buffers to produce a store and display signal when the periods are substantially the same and an add signal when the periods are substantially different;

a third buffer for storing said time interval in said first buffer in response to said store and display signal;

means for adding the stored periods in said first and second buffers in response to said add signal, said comparing means then comparing the period in said third buffer with the sum to produce another display signal when said sum and said period stored in said third buffer are substantially the same and disregarding said sum when said sum and said period in said third buffer are substantially different; and display means for producing a display of the period in said first buffer in response to said store and display signal and a display of the sum in response to said another display signal.

3. A detector as in claim 1 wherein display means includes a time-frequency converter for receiving said display and store signal and said another display signal, a display driver connected to the output to said time-frequency converter and a display connected to the output to said display driver.

4. A detector as in claim 2 wherein said determining and storing means includes means for detecting negative-going transitions and a timer for determining the intervals between successive transitions.

5. A detector as defined in claim 2, said filtering means including a first digital filter having a first passband for filtering said digital signals and producing filtered digital signals and a second digital filter having a second passband for filtering said filtered digital signals for producing twice filtered digital signals.

6. A detector as defined in claim 5, said first passband being about 16–42 Hz and said second passband being about 0–3 Hz.

7. A detector as defined in claim 2 wherein said determining and storing means includes:

means for determining the absolute value of the amplitude of said filtered electrical signals and means for comparing the absolute value of the amplitude of said filtered electrical signals at small time intervals and producing an output signal indicative of a heart sound at the first occurrence of a signal having a reduced amplitude following a sequence of signals having increasing amplitudes.

* * * * *